(12) United States Patent
Heidemann et al.

(10) Patent No.: US 7,291,759 B2
(45) Date of Patent: Nov. 6, 2007

(54) OLIGOMERIZATION OF ALKENES IN A PLURALITY OF SUCCESSIVE HETEROGENEOUS CATALYST ZONES

(75) Inventors: Thomas Heidemann, Viernheim (DE); Ursula Siebenhaar, Limburgerhof (DE)

(73) Assignee: BASF Aktiengesellschaft (DE)

( * ) Notice: Subject to any disclaimer, the term of this patent is extended or adjusted under 35 U.S.C. 154(b) by 494 days.

(21) Appl. No.: 10/518,449

(22) PCT Filed: Jun. 27, 2003

(86) PCT No.: PCT/EP03/06838

§ 371 (c)(1),
(2), (4) Date: Dec. 20, 2004

(87) PCT Pub. No.: WO2004/005224

PCT Pub. Date: Jan. 15, 2004

(65) Prior Publication Data

US 2005/0203325 A1    Sep. 15, 2005

(30) Foreign Application Priority Data

Jul. 3, 2002    (DE) ................ 102 29 763

(51) Int. Cl.
*C07C 2/02* (2006.01)
(52) U.S. Cl. ............ 585/531; 585/515; 585/526; 585/530
(58) Field of Classification Search ........... 585/526, 585/531, 530, 515
See application file for complete search history.

(56) References Cited

U.S. PATENT DOCUMENTS

| | | | |
|---|---|---|---|
| 2,794,842 A | 6/1957 | Hogan et al. | |
| 3,959,400 A | 5/1976 | Lucki | |
| 4,511,750 A | 4/1985 | Miller | |
| 5,849,972 A | 12/1998 | Vicari et al. | |
| 5,883,036 A | 3/1999 | Fujie et al. | |
| 6,846,965 B1* | 1/2005 | Schulz et al. | ........ 585/510 |
| 2003/0130550 A1 | 7/2003 | Schulz et al. | |

FOREIGN PATENT DOCUMENTS

| | | |
|---|---|---|
| DE | 199 22 038 | 11/2000 |
| DE | 199 57 173 | 5/2001 |

(Continued)

OTHER PUBLICATIONS

U.S. Appl. No. 09/959,792.

(Continued)

*Primary Examiner*—Glenn Caldarola
*Assistant Examiner*—In Suk Bullock
(74) *Attorney, Agent, or Firm*—Connolly Bove Lodge & Hutz LLP

(57) ABSTRACT

Process for oligomerizing an alkene stream over a solid catalyst comprising sulfur and nickel, in which the oligomerization is carried out in two or more successive catalyst zones and the molar ratio of sulfur to nickel in the first catalyst zone is less than 0.5 and that in the last catalyst zone is 0.5 or more and, in the case of further catalyst zones between the first and last catalyst zones, the molar ratio of sulfur to nickel in each catalyst zone is not less than that in the immediately preceding catalyst zone, based on the main flow direction of the feed stream.

16 Claims, 1 Drawing Sheet

FOREIGN PATENT DOCUMENTS

Figure 1:
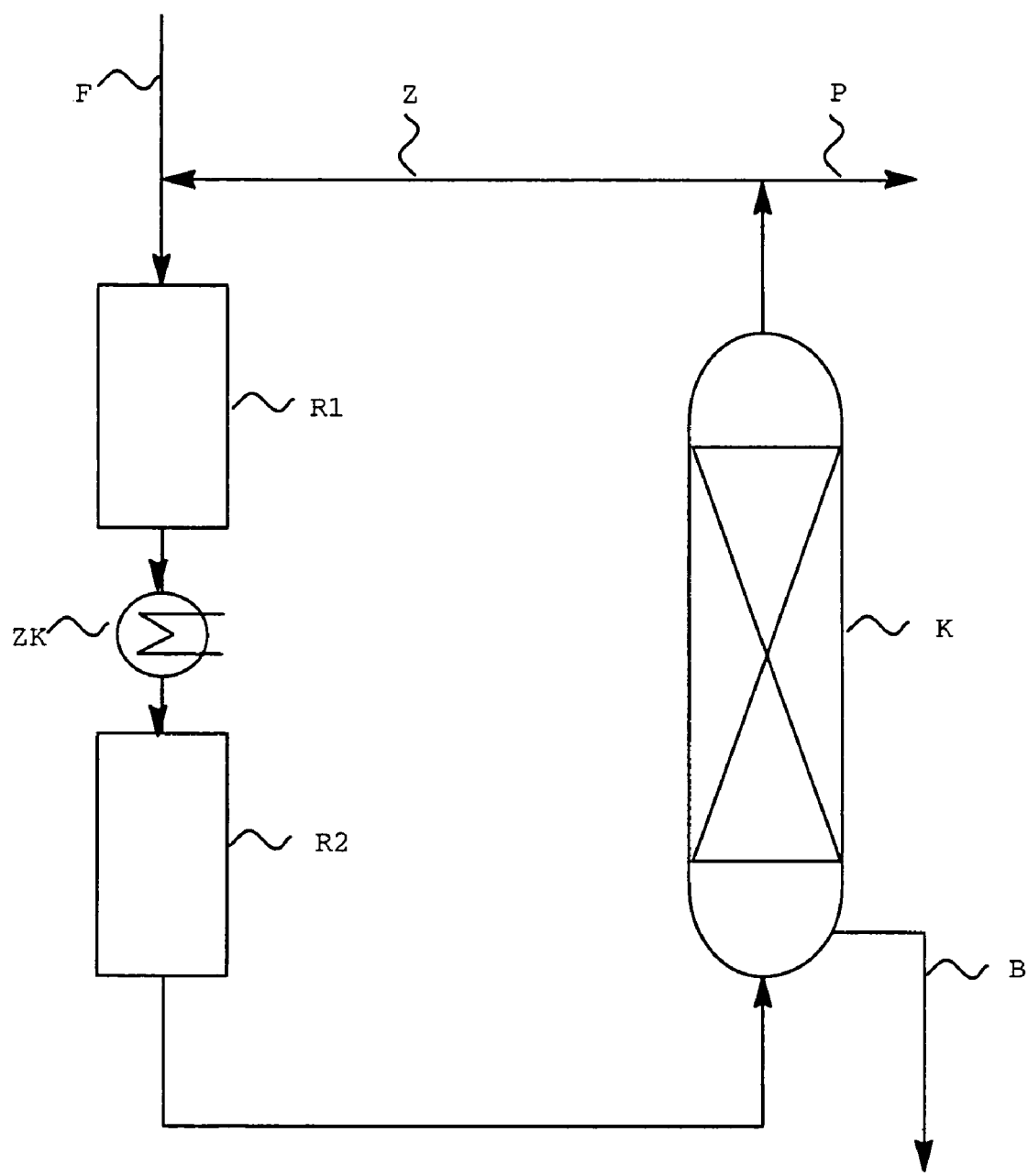

| | | |
|---|---|---|
| EP | 0 272 970 | 6/1988 |
| FR | 2 641 477 | 7/1990 |
| WO | WO-95/14647 | 6/1995 |
| WO | WO-99/25668 | 5/1999 |
| WO | WO 0069795 | 11/2000 |
| WO | WO-01/37989 | 5/2001 |
| WO | WO-01/72670 | 10/2001 |

OTHER PUBLICATIONS

U.S. Appl. No. 10/129,981.

* cited by examiner

OLIGOMERIZATION OF ALKENES IN A PLURALITY OF SUCCESSIVE HETEROGENEOUS CATALYST ZONES

RELATED APPLICATIONS

This application is a national stage application (under 35 U.S.C. 371) of PCT/EP2003/006838 filed Jun. 27, 2003 which claims benefit to German application Serial No. 102 29 763.0 filed Jul. 3, 2002.

The present invention relates to a process for oligomerizing an alkene stream over a solid catalyst comprising sulfur and nickel.

Alkenes having from 2 to 6 carbon atoms and mixtures thereof, in particular alkenes having 4 carbon atoms, are available in large quantities both from FCC plants and from steam crackers. The $C_4$ fraction, i.e. the mixture of butenes and butanes, obtained in each case is, after the isobutene has been separated off, particularly well suited to the preparation of oligomers, in particular octenes and dodecenes. Both the octenes and the dodecenes are, after hydroformylation and subsequent hydrogenation to form the corresponding alcohols, used, for example, for the preparation of plasticizers or surfactant alcohols.

In the case of plasticizer alcohols, the degree of branching generally has an effect on the properties of the plasticizer. The degree of branching is described by the iso index, which indicates the mean number of methyl branches in the respective fraction. Thus, for example, n-octenes contribute 0, methylheptenes contribute 1 and dimethylhexenes contribute 2 to the iso index of a $C_8$ fraction. The lower the iso index, the more linear are the molecules in the respective fraction. The higher the linearity, i.e. the lower the iso index, the higher the yields in the hydroformylation and the better the properties of the plasticizer prepared therewith. A lower iso index leads, for example, in the case of phthalate plasticizers, to a reduced volatility and in the case of flexible PVC formulations containing these plasticizers, to improved cold fracture behavior.

The conversion of alkenes into low molecular weight oligomers over nickel- and sulfur-containing heterogeneous catalysts is prior art. Catalysts suitable for this purpose are described below.

However, the previously known processes of this type have the disadvantage that because of the decreasing alkene content of the feed stream in the direction of the reactor outlet, a satisfactory conversion of the alkenes into relatively unbranched alkenes has hitherto generally only been possible if the temperature is increased in the outlet end of the catalyst bed or if a more active catalyst is used in this region or the total catalyst volume is increased.

It is an object of the present invention to remedy these disadvantages of the prior art by means of an improved catalyst bed.

We have found that this object is achieved by a process for oligomerizing an alkene stream over a solid catalyst comprising sulfur and nickel, wherein the oligomerization is carried out in two or more successive catalyst zones and the molar ratio of sulfur to nickel in the first catalyst zone is less than 0.5 and that in the last catalyst zone is 0.5 or more and, in the case of further catalyst zones between the first and last catalyst zones, the molar ratio of sulfur to nickel in each catalyst zone is not less than that in the immediately preceding catalyst zone, based on the main flow direction of the feed stream.

For the purposes of the present invention, the term "oligomers" refers to dimers, trimers and higher oligomers of the alkenes. The process of the present invention is particularly useful for preparing dimers of these alkenes.

As starting materials, preference is given to using alkenes having from 2 to 6 carbon atoms, mixtures of such alkenes with one another or mixtures of such alkenes with alkanes. The oligomerization process of the present invention is particularly suitable for the reaction of mixtures of alkenes having 3 and in particular 4 carbon atoms, especially hydrocarbon streams which comprise 1-butene and/or 2-butene and one or more butanes and are essentially free of isobutene.

The reactor is generally a (cylindrical) tube reactor. As an alternative, the reactor used can be a reactor cascade comprising a plurality of, preferably two or three, such tube reactors (subreactors) connected in series, as is known, for example, from WO-A 99/25668 or WO-A 01/72670.

The catalysts over which the oligomerization is carried out are heterogeneous catalysts comprising sulfur and nickel. They are generally known, for example from FR-A 2 641 477, EP-A 272 970, WO-A 95/14647 and WO-A 01/37989, U.S. Pat. No. 2,794,842, U.S. Pat. No. 3,959,400, U.S. Pat. No. 4,511,750 and U.S. Pat. No. 5,883,036, which are hereby fully incorporated by reference in respect of the sulfur- and nickel-containing catalysts disclosed therein. Particularly useful catalysts of this type are those which lead to a low degree of branching in the oligomers obtainable therewith, especially those described in WO-A 95/14647, WO-A 01/37989 and the documents of the prior art cited in this context in these two documents.

The totality of the catalyst over which the starting material passes in the reactor will hereinafter be referred to as the fixed catalyst bed. If a reactor cascade is employed, the fixed catalyst bed is generally distributed over all the subreactors of the cascade.

The total fixed catalyst bed is, according to the present invention, divided into two or more successive catalyst zones. In this context, a catalyst zone is a section of the fixed catalyst bed in the flow direction of the feed. Such a catalyst zone has a specific sulfur-to-nickel ratio compared to the adjacent catalyst zone(s), especially, when the catalyst zone is located between two other catalyst zones, these two adjacent catalyst zones. In the case of a reactor cascade, a catalyst zone can be located within a single subreactor or can be distributed continuously over two or more successive subreactors, without the fixed catalyst bed in the first and last subreactor having to be made up entirely of this catalyst zone.

The catalysts of the first and last catalyst zones in particular can each be accommodated in a single reactor or in a cascade of reactors for the purposes of the reaction.

The feed stream can also be divided and the substreams obtained in this way can be fed to the fixed catalyst bed at different places, for instance when using a reactor cascade at the points between the individual reactors. It is also possible for a substream of the total feed stream to be fed in before the beginning of a catalyst zone or, particularly when a catalyst zone extends from one subreactor to the next in a cascade, at the point at which the catalyst zone is divided between the two subreactors.

As catalysts for the first catalyst zone, in which the molar ratio of sulfur to nickel is less than 0.5, preference is given to using catalysts of this type as described in WO-A 95/14647 or WO-A 01/37989.

As catalysts for the last catalyst zone, in which the molar ratio of sulfur to nickel is 0.5 or more, preference is given to using catalysts of this type as described in FR-A 2 641 477, EP-A 272 970, U.S. Pat. No. 3,959,400 or U.S. Pat. No.

4,511,750, in particular those having a molar ratio of sulfur to nickel of more than 0.8 and very particularly preferably those having a molar ratio of sulfur to nickel of greater than or equal to 1.

The process of the present invention is preferably carried out over a fixed catalyst bed in which the molar ratio of sulfur to nickel in the first catalyst zone is less than 0.4 and that in the last catalyst zone is more than 0.6.

In a further, preferred embodiment, the process of the present invention is carried out over a fixed catalyst bed in which the molar ratio of sulfur to nickel in the first catalyst zone is less than 0.4 and that in the last catalyst zone is more than 0.8.

In a further, preferred embodiment, the process of the present invention is carried out over a fixed catalyst bed in which the molar ratio of sulfur to nickel in the first catalyst zone is less than 0.4 and that in the last catalyst zone is equal to or more than 1.

The second and all further catalyst zones of the fixed catalyst bed will hereinafter be referred to as "remaining catalyst zones" to distinguish them from the first catalyst zone.

The process of the present invention is preferably carried out in such a way that the alkenes of the feed stream are reacted to an extent of from 50 to 99%, preferably from 65 to 99%, especially from 80 to 99% and in particular from 90 to 99%, in the first catalyst zone in which the molar ratio of sulfur to nickel is less than 0.5.

Furthermore, the process of the present invention is preferably carried out in such a way that the alkenes of the feed stream are reacted to an extent of from 10 to 99%, preferably from 50 to 99%, in the remaining catalyst zones.

In a further, preferred embodiment, the process of the present invention is carried out in such a way that the alkenes in the feed stream are reacted to an extent of from 50 to 99% in the first catalyst zone and the alkenes remaining unreacted after this first catalyst zone are reacted to an extent of from 10 to 99% in the remaining catalyst zones.

In a further, preferred embodiment, the process of the present invention is carried out in such a way that the alkenes in the feed stream are reacted to an extent of from 65 to 99% in the first catalyst zone and the alkenes remaining unreacted after this first catalyst zone are reacted to an extent of from 10 to 99% in the remaining catalyst zones.

In a further, preferred embodiment, the process of the present invention is carried out in such a way that the alkenes in the feed stream are reacted to an extent of from 80 to 95% in the first catalyst zone and the alkenes remaining unreacted after this first catalyst zone are reacted to an extent of from 10 to 99% in the remaining catalyst zones.

In a further, preferred embodiment, the process of the present invention is carried out in such a way that the alkenes in the feed stream are reacted to an extent of from 80 to 95% in the first catalyst zone and the alkenes remaining unreacted after this first catalyst zone are reacted to an extent of from 50 to 99% in the remaining catalyst zones.

Furthermore, the process of the present invention is preferably carried out in such a way that a total conversion of the alkenes in the feed stream of more than 91%, preferably more than 95% and in particular more than 97%, is achieved over all catalyst zones.

The oligomerization reaction is generally carried out at from 30 to 280° C., preferably from 30 to 190° C. and in particular from 40 to 130° C., and a pressure of generally from 1 to 300 bar, preferably from 5 to 100 bar and in particular from 10 to 50 bar. The pressure is advantageously selected so that the feed is supercritical and in particular liquid at the temperature set. Different reaction conditions in respect of pressure and/or temperature within these pressure and temperature ranges can be set in the individual tube reactors of a reactor cascade.

The oligomerization process of the present invention can be carried out adiabatically or isothermally.

Otherwise, the way of carrying out the process is sufficiently well known to a person skilled in the art, especially from WO-A 99/25668 and WO-A 01/72670, whose relevant contents are hereby fully incorporated by reference.

After leaving the reactor, the oligomers formed are separated in a manner known per se from the unreacted hydrocarbons and the latter are, if desired, returned to the process (cf., for example, WO-A 95/14647). The separation is generally carried out by fractional distillation.

Compared to known processes of this type, the process of the present invention leads to a high alkene conversion combined with a low degree of branching of the oligomers obtainable in this way. This effect has hitherto generally been able to be achieved only by increasing the temperature in the later part of the catalyst bed or by using a more active catalyst in this region or by means of an increased total volume of catalyst because of the decreasing alkene content of the gas stream in the direction of the reactor outlet.

EXAMPLES

I. Catalysts
The Ni(NO$_3$)$_2$.6 H$_2$O used came from Fluka.
Catalyst "1a" (S:Ni ratio=0)
As described in DE-A 43 39 713, Example 1, a sulfur-free catalyst was prepared from 50% by weight of NiO, 37% by weight of SiO$_2$ and 13% by weight of TiO$_2$.

Catalyst "1b" (S:Ni ratio=0.34)
γ-aluminum oxide of the grade "D10-10" from BASF AG (3 mm star extrudates, BET surface area: 202 m$^2$/g, water absorption capacity: 0.76 ml/g, loss on ignition: 1.6% by weight) was used as support.

200 g of this support were impregnated at room temperature with 125 ml of a solution of 125 mmol of 96% strength H$_2$SO$_4$ and 361 mmol of 97% strength Ni(NO$_3$)$_2$.6 H$_2$O in water while stirring. The catalyst obtained in this way was dried in air at 120° C. for 10 hours and calcined in air at 500° C. for 2 hours. The proportion of nickel ("Ni") was then determined as 9.04% by weight and that of sulfur ("S") was determined as 1.67% by weight, in each case based on the total weight of the catalyst obtained, and the molar ratio of sulfur to nickel ("S:Ni") in the catalyst was determined as 0.34.

The sulfur content of the finished catalyst was determined by quantitative infrared analysis of the sulfur dioxide formed on combustion of the catalyst. The nickel content could be obtained by ICP-mass spectrometry.

Catalyst "1c" (S:Ni ratio=1)
γ-aluminum oxide of the grade "D10-10" from BASF AG (4 mm extrudates, BET surface area: 210 m$^2$/g, water absorption capacity: 0.73 ml/g, loss on ignition: 1.8% by weight) was used as support.

400 g of this support were impregnated at room temperature with a solution of 184 g of NiSO$_4$.6 H$_2$O in water while stirring. The volume of the water used was chosen in accordance with the water absorption capacity of the support. The catalyst obtained in this way was dried in air at 120° C. for 16 hours and calcined in air at 500° C. for 2 hours. The proportion of nickel ("Ni") was then determined as 7.9% by weight and that of sulfur ("S") was determined as 4.32% by weight, in each case based on the total weight of the catalyst obtained, and the molar ratio of sulfur to nickel ("S:Ni") in the catalyst was determined as 1.

II. Oligomerizations

A) Apparatus

FIG. 1 schematically shows an apparatus in which the process of the present invention was, by way of example, carried out continuously at 30 bar. The alkene-containing stream (hereinafter referred to as the "Feed") was fed via F into the adiabatic subreactor R1 and from there conveyed via intermediate cooling ZK to the adiabatic subreactor R2. The subreactors had a length of 4 m and a diameter of 0.08 m, so that they each had a volume of 20 liters; when only 20 liters of catalyst were used, all the catalyst was placed in one of the two subreactors, while the second subreactor contained steatite spheres as inert material. The output from the reactor R2 was worked up by distillation in the column K and the oligomeric product was taken off as bottoms via B. The stream taken from the top of the column K was partly recirculated via Z to the reactor R1, and the other part of this stream was discharged from the apparatus via P (as purge stream).

The reaction pressure, which was higher than the pressure at which the raffinate II was supplied, was generated by means of an upstream reactor feed pump and was regulated by means of customary pressure maintenance devices downstream of the reactor.

The butene/butane mixtures shown in table 1 were used.

TABLE 1

(FIGURES are in % by weight based on the total feed stream F)

| Mixture | n-butenes | butanes | isobutene |
|---|---|---|---|
| A | 78 | 19.7 | 2.3 |
| B | 54.2 | 44.8 | 1 |
| C | 56.9 | 42.3 | 0.8 |
| D | 55.8 | 44.5 | 0.7 |
| E | 26.8 | 72.9 | 0.3 |
| F | 26.4 | 73.2 | 0.4 |

B) Experimental Procedure

B.1) Reactions Over a Single Catalyst Zone

The butene/butane mixtures shown in table 1 were passed at the mean temperature T over the volume Vol of the catalyst Cat located in the apparatus shown in FIG. 1. The output from the reactor was isolated and analyzed. Further details of the experimental parameters and the results of the experiments are shown in table 2.

B.2) Conversion of the Results from B.1 to 2 and 3 Catalyst Zones

The results from section B.1 were summarized mathematically. Table 3 shows the results obtained in this way for the sequences according to the present invention (No. 1, 4 and 5) of catalyst zones and for the sequences not according to the present invention (No. 2, 3, 6 and 7) determined for comparative purposes.

It can be seen from the experimental results that combination of two or three catalyst zones to form a fixed catalyst bed in accordance with the present invention gives, at comparable alkene conversions and iso indices of the octenes, a space-time yield in respect of octenes and dodecenes which is from 15 to 33% higher than that obtained in the reaction over catalyst beds which are not in accordance with the present invention. In addition, these results can be obtained at lower reaction temperatures over the catalyst, which has been found on the basis of experience to lead to an increased active life of the catalyst (operating life). This also increases the temperature interval in which the conversion can be increased by increasing the temperature.

TABLE 2

| Mixture | Cat | Vol [l] | T [° C.] | Octenes [% by weight] | Dodecenes [% by weight] | C16+-alkenes [% by weight] | C[%] | Iso I |
|---|---|---|---|---|---|---|---|---|
| A | 1a | 40 | 60 | 83.7 | 13.3 | 3 | 70.5 | 0.95 |
| B | 1b | 40 | 60 | 92.9 | 5.2 | 1.9 | 67.6 | 1.1 |
| C | 1b | 40 | 80 | 88.7 | 9.1 | 2.2 | 70.2 | 1.15 |
| D | 1c | 20 | 70 | 75.3 | 20.6 | 4.1 | 70.4 | 1.68 |
| E | 1a | 40 | 90 | 82.4 | 13.8 | 3.8 | 68.1 | 1.01 |
| F | 1c | 20 | 80 | 74.8 | 20.7 | 4.5 | 70 | 1.68 |

| | |
|---|---|
| Mixture | Mixture having the composition shown in table 1 |
| Cat | Catalyst used |
| Vol | Catalyst volume |
| T | Mean reaction temperature in the catalyst zone |
| C16+-alkenes | Alkenes having 16 or more carbon atoms present |
| C | Total butene conversion |
| Iso I | Iso index of the C8 fraction of the oligomerization product |

TABLE 3

| | Catalyst zone 1 | | | | Catalyst zone 2 | | | | Catalyst zone 3 | | | | | | | |
|---|---|---|---|---|---|---|---|---|---|---|---|---|---|---|---|---|
| No. | Cat | S:Ni | Vol [l] | T [° C.] | Cat | S:Ni | Vol [l] | T [° C.] | Cat | S:Ni | Vol [l] | T [° C.] | C | Y | STY | Iso I |
| 1 (According to the present invention) | 1a | 0 | 40 | 60 | 1c | 1 | 20 | 70 | — | — | — | — | 91.3 | 14.4 | 0.24 | 1.17 |
| 2 (Comparison 1) | 1b | 0.34 | 40 | 60 | 1b | 0.34 | 40 | 80 | — | — | — | — | 90.3 | 14.1 | 0.18 | 1.12 |
| 3 (Comparison 2) | 1a | 0 | 40 | 60 | 1b | 0.34 | 40 | 80 | — | — | — | — | 91.2 | 14.5 | 0.18 | 1.01 |
| 4 (According to the present invention) | 1b | 0.34 | 40 | 60 | 1b | 0.34 | 40 | 80 | 1c | 1 | 20 | 80 | 97.1 | 15.2 | 0.15 | 1.15 |
| 5 (According to the present invention) | 1a | 0 | 40 | 60 | 1b | 0.34 | 40 | 80 | 1c | 1 | 20 | 80 | 97.4 | 15.5 | 0.16 | 1.06 |

TABLE 3-continued

| | | | | | | | | | | | | | | | | |
|---|---|---|---|---|---|---|---|---|---|---|---|---|---|---|---|---|
| 6 (Comparison 3) | 1b | 0.34 | 40 | 60 | 1b | 0.34 | 40 | 80 | 1a | 0 | 40 | 90 | 96.9 | 15.2 | 0.13 | 1.11 |
| 7 (Comparison 4) | 1a | 0 | 40 | 60 | 1b | 0.34 | 40 | 80 | 1a | 0 | 40 | 90 | 97.2 | 15.6 | 0.13 | 1.01 |

Cat    Catalyst used
S:Ni    Molar ratio of sulfur to nickel in the catalyst
Vol    Catalyst volume
T    Mean reaction temperature in the catalyst zone
C    Total butene conversion
Y    Yield of alkenes having 8 or 12 carbon atoms
STY    Mean space-time yield, expressed in kilograms of alkenes having 8 or 12 carbon atoms per liter of catalyst and hour
Iso I    Iso index of the C8 fraction of the oligomerization product

The invention claimed is:

1. A process for oligomerizing an alkene stream over a solid catalyst comprising sulfur and nickel, wherein the oligomerization is carried out in two or more successive catalyst zones and the molar ratio of sulfur to nickel in the first catalyst zone is less than 0.5 and that in the last catalyst zone is 0.5 or more and, in the case of further catalyst zones between the first and last catalyst zones, the molar ratio of sulfur to nickel in each catalyst zone is not less than that in the preceding catalyst zone, based on the main flow direction of the feed stream.

2. The process according to claim 1, wherein the molar ratio of sulfur to nickel in the first catalyst zone is less than 0.4 and that in the last catalyst zone is more than 0.6.

3. The process according to claim 1, wherein a catalyst obtainable by a process in which aluminum oxide is treated with a nickel compound and a sulfur compound, either simultaneously or firstly with the nickel compound and then with the sulfur compound, and the catalyst obtained in this way is subsequently dried and calcined and a molar ratio of sulfur to nickel of from 0.25:1 to 0.38:1 is in this way set in the finished catalyst is used.

4. The process according to claim 1, wherein a catalyst which consists essentially of nickel oxide, silicon dioxide, titanium dioxide and/or zirconium dioxide and, if appropriate, aluminum oxide and has a content, after subtraction of the loss on ignition after heating at 900° C., of nickel oxide, calculated as NiO, of from 10 to 70% by weight, from 5 to 30% by weight of titanium dioxide and/or zirconium dioxide, from 0 to 20% by weight of aluminum oxide, from 20 to 40% by weight of silicon dioxide and from 0.01 to 1% by weight of an alkali metal oxide, with the proviso that the proportions of the individual components add up to 100%, and is obtainable by precipitation of an aluminum-free nickel salt solution or a nickel salt solution containing a dissolved aluminum salt at a pH of from 5 to 9 by addition of this nickel salt solution to an alkali metal water glass solution containing solid titanium dioxide and/or zirconium dioxide, drying and heating of the resulting precipitate at from 350 to 650° C. is used.

5. The process according to claim 1, wherein the alkene stream used is a mixture of alkenes and alkanes having from 2 to 6 carbon atoms.

6. The process according to claim 1, wherein the alkene stream used is a mixture of butenes and butanes.

7. The process according to claim 1, wherein the alkenes of the alkene stream are reacted to an extent of from 65 to 99% in the first catalyst zone and the alkenes remaining unreacted after this first catalyst zone are reacted to an extent of from 10 to 99% in the remaining catalyst zones.

8. The process according to claim 2, wherein a catalyst obtainable by a process in which aluminum oxide is treated with a nickel compound and a sulfur compound, either simultaneously or firstly with the nickel compound and then with the sulfur compound, and the catalyst obtained in this way is subsequently dried and calcined and a molar ratio of sulfur to nickel of from 0.25:1 to 0.38:1 is in this way set in the finished catalyst is used.

9. The process according to claim 2, wherein a catalyst which consists essentially of nickel oxide, silicon dioxide, titanium dioxide and/or zirconium dioxide and, if appropriate, aluminum oxide and has a content, after subtraction of the loss on ignition after heating at 900° C., of nickel oxide, calculated as NiO, of from 10 to 70% by weight, from 5 to 30% by weight of titanium dioxide and/or zirconium dioxide, from 0 to 20% by weight of aluminum oxide, from 20 to 40% by weight of silicon dioxide and from 0.01 to 1% by weight of an alkali metal oxide, with the proviso that the proportions of the individual components add up to 100%, and is obtainable by precipitation of an aluminum-free nickel salt solution or a nickel salt solution containing a dissolved aluminum salt at a pH of from 5 to 9 by addition of this nickel salt solution to an alkali metal water glass solution containing solid titanium dioxide and/or zirconium dioxide, drying and heating of the resulting precipitate at from 350 to 650° C. is used.

10. The process according to claim 9, wherein the alkene stream used is a mixture of alkenes and alkanes having from 2 to 6 carbon atoms.

11. The process according to claim 10, wherein the alkene stream used is a mixture of butenes and butanes.

12. The process according to claim 11, wherein the alkenes of the alkene stream are reacted to an extent of from 65 to 99% in the first catalyst zone and the alkenes remaining unreacted after this first catalyst zone are reacted to an extent of from 10 to 99% in the remaining catalyst zones.

13. The process according to claim 1, wherein the process is carried out over a fixed catalyst bed in which the molar ratio of sulfur to nickel in the first catalyst zone is less than 0.4 and that in the last catalyst zone is more than 0.8.

14. The process according to claim 2, wherein the process is carried out over a fixed catalyst bed in which the molar ratio of sulfur to nickel in the first catalyst zone is less than 0.4 and that in the last catalyst zone is more than 1.

15. The process according to claim 1, wherein the alkenes of the alkene stream are reacted to an extent of from 80 to 99% in the first catalyst zone and the alkenes remaining unreacted after this first catalyst zone are reacted to an extent of from 10 to 99% in the remaining catalyst zones.

16. The process according to claim 1, wherein the alkenes of the alkene stream are reacted to an extent of from 90 to 99% in the first catalyst zone and the alkenes remaining unreacted after this first catalyst zone are reacted to an extent of from 50 to 99% in the remaining catalyst zones.

* * * * *

UNITED STATES PATENT AND TRADEMARK OFFICE
CERTIFICATE OF CORRECTION

PATENT NO. : 7,291,759 B2  Page 1 of 1
APPLICATION NO. : 10/518449
DATED : November 6, 2007
INVENTOR(S) : Thomas Heidemann et al.

It is certified that error appears in the above-identified patent and that said Letters Patent is hereby corrected as shown below:

In the Claims:

In Claim 4,

Column 7 and lines 38-39, "if appropriate," should read -- optionally --.

Column 7 and line 47, "obtainable" should read -- obtained --.

In Claim 9,

Column 8 and lines 21-22, "if appropriate," should read -- optionally --.

Column 8 and line 30, "obtainable" should read -- obtained --.

Signed and Sealed this

First Day of April, 2008

JON W. DUDAS
*Director of the United States Patent and Trademark Office*